(12) United States Patent
Jones

(10) Patent No.: US 8,061,216 B2
(45) Date of Patent: Nov. 22, 2011

(54) ASPIRATION FLOW MESUREMENT SYSTEM WITH FLOW SIGNAL AIR BUBBLE FILTER

(75) Inventor: Ross Peter Jones, Cambridge (GB)

(73) Assignee: Bausch & Lomb Incorporated, Rochester, NY (US)

( * ) Notice: Subject to any disclaimer, the term of this patent is extended or adjusted under 35 U.S.C. 154(b) by 160 days.

(21) Appl. No.: 12/270,209

(22) Filed: Nov. 13, 2008

(65) Prior Publication Data
US 2009/0158812 A1   Jun. 25, 2009

Related U.S. Application Data

(60) Provisional application No. 61/016,001, filed on Dec. 21, 2007.

(51) Int. Cl.
*G01F 1/74* (2006.01)
*A61M 1/00* (2006.01)

(52) U.S. Cl. .............. 73/861.04; 604/317; 73/861.08; 702/45

(58) Field of Classification Search .................. None
See application file for complete search history.

(56) References Cited

U.S. PATENT DOCUMENTS

| | | | |
|---|---|---|---|
| 3,693,613 A | 9/1972 | Kelman | |
| 5,005,425 A * | 4/1991 | Ohmae | 73/861.22 |
| 5,646,344 A * | 7/1997 | Konzelmann | 73/204.18 |
| 6,470,868 B2 * | 10/2002 | Nakagawa et al. | 123/673 |
| 6,505,519 B2 * | 1/2003 | Henry et al. | 73/861.356 |
| 6,568,281 B1 * | 5/2003 | Sato et al. | 73/861.27 |
| 6,599,277 B2 | 7/2003 | Neubert | 604/317 |
| 6,634,237 B2 | 10/2003 | Neubert | 73/861.12 |
| 6,758,102 B2 * | 7/2004 | Henry et al. | 73/861.356 |
| 7,650,225 B2 * | 1/2010 | Nakagawa et al. | 701/109 |

FOREIGN PATENT DOCUMENTS

| | | |
|---|---|---|
| JP | H5-23394 | 2/1993 |
| WO | WO 96/12511 A1 | 5/1996 |
| WO | WO 00/28890 A1 | 5/2000 |

OTHER PUBLICATIONS

International Search Report (PCTISA/210) and Written Opinion (PCT/ISA/237) mailed on May 15, 2009.

* cited by examiner

*Primary Examiner* — Harshad Patel
(74) *Attorney, Agent, or Firm* — Jeffrey B. Powers

(57) ABSTRACT

In an aspiration flow measurement system, a flow channel is provided for receiving an aspiration fluid flow therethrough. The flow measurement system further includes an aspiration flow measurement chamber and a flow sensor that is configured to generate a raw signal indicative of the rate of fluid flow through the flow channel. A control system is configured to monitor the signals indicating the flow through the flow measurement chamber, and to determine when a value of the raw signal is indicative of a disruption caused by the presence of an air bubble, wherein the control system generates a filtered signal of the flow rate that is exclusive of any signal values that are indicative of a disruption.

20 Claims, 8 Drawing Sheets

US 8,061,216 B2

ASPIRATION FLOW MESUREMENT SYSTEM WITH FLOW SIGNAL AIR BUBBLE FILTER

CROSS-REFERENCE TO RELATED APPLICATIONS

This application claims priority to U.S. Provisional Patent Application Ser. No. 61/016,001, filed Dec. 21, 2007, the entire disclosure of which is incorporated herein.

FIELD

The present invention relates to sensing an aspiration flow rate in a surgical pump system. More particularly, the present application is directed towards flow measurement in ophthalmic microsurgical pump systems.

BACKGROUND

The statements in this section merely provide background information related to the present disclosure and may not constitute prior art.

The flow and flow rate of fluids through an aspiration tube is of interest during operations, including ophthalmic operations. During ophthalmic microsurgery, small probes are inserted into an operative site to remove tissues and fluids may be infused into the operative site through the probes. Infusion fluids may also be aspirated from the site. Surgical cassettes may also be coupled to surgical probes, to provide for collection of aspirated fluids. Measurement of the surgical aspiration flow rate may be valuable in that it can provide for safe control of the ophthalmic surgical equipment. However, passage of air bubbles, among other factors, within the aspiration measurement devices can make measurement of the flow rate difficult to achieve.

Therefore, it would be desirable to incorporate air filtering or diverting means into a disposable surgical cassette to permit accurate measurement of flow rate by removing or greatly reducing any effect of the air bubbles.

SUMMARY

The present disclosure relates to ophthalmic surgical systems in which an aspiration flow measurement system is provided. According to one embodiment of an aspiration flow measurement system, a flow channel is provided for receiving an aspiration fluid flow therethrough. The flow measurement system further includes an aspiration flow measurement apparatus that is configured to generate a signal indicative of the rate of fluid flow through the flow channel. A control system is configured to monitor the signals generated by the aspiration flow measurement apparatus, and to determine when a signal value is indicative of a disruption caused by the presence of an air bubble, wherein the control system generates a filtered signal indicative of the flow rate that is exclusive of any signal values that are indicative of a disruption.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
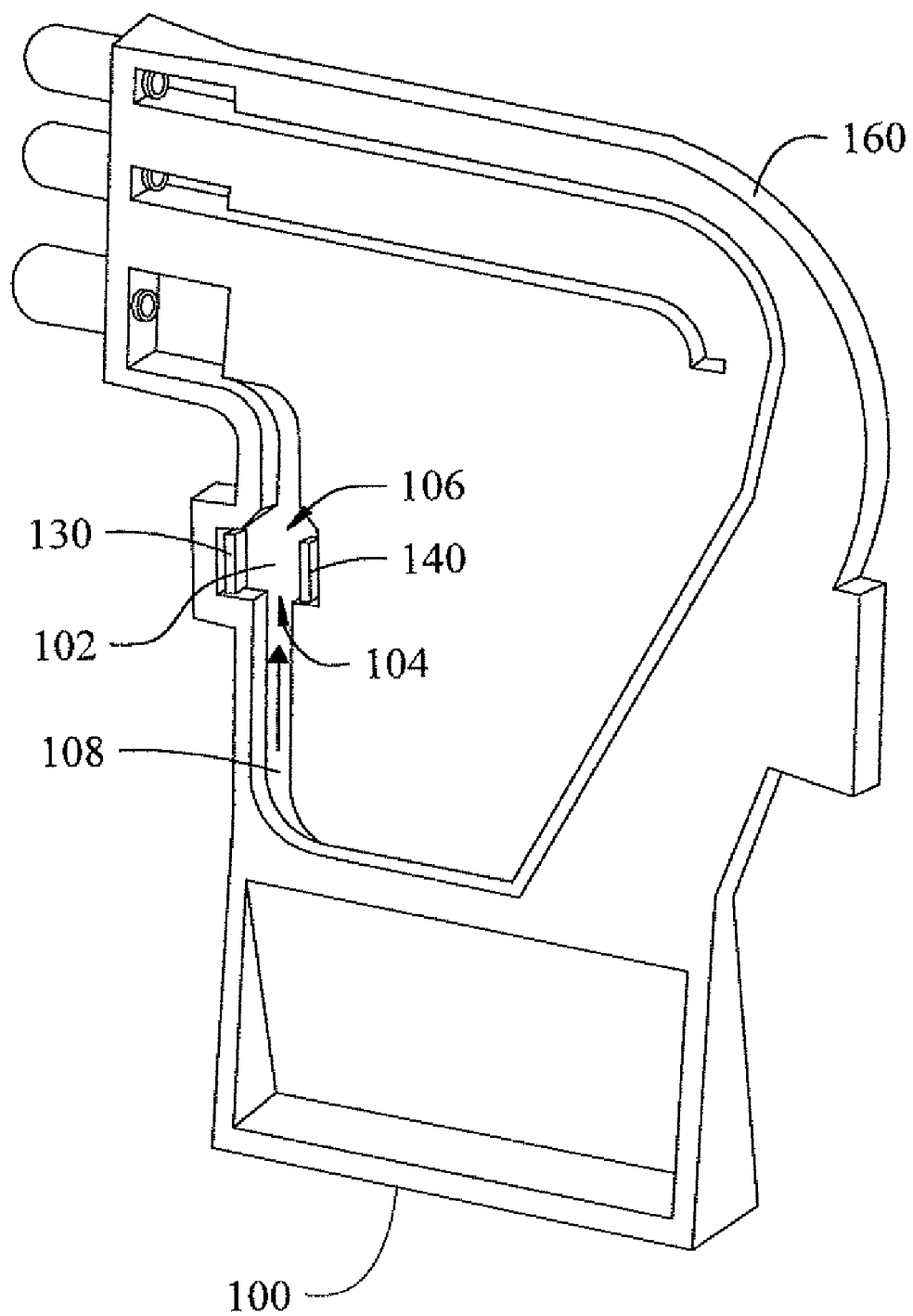
FIG. 1 is a cut-away perspective view of part of a housing for one embodiment of a flow device for an ophthalmic surgical system in accordance with the principles of the present disclosure.

The following description is merely exemplary in nature and is not intended to limit the present disclosure, application, or uses. It should be understood that throughout the drawings, corresponding reference numerals indicate like or corresponding parts and features.

In the various embodiments, an aspiration flow measurement control means for an ophthalmic surgical system is provided that is configured to filter out the effect of air bubbles on flow measurement. Ophthalmic surgical systems may include a cassette in which an aspiration flow measurement system may be incorporated. Ophthalmic systems may also have feedback control loops, where a signal from a flow measurement means in the aspiration flow path is compared to a desired flow rate. Signals are then sent to a vacuum control device, such as a proportional valve, to increase or decrease the flow rate. An example of a portion of such a cassette or flow control system is shown in FIG. 1. A partial cassette housing 100 includes an electrode terminal chamber 102 having an inlet 104 and an outlet 106. The portion of the cassette not shown is essentially the collection container portion and tubing connections, which can be any known cassette for ophthalmic surgery. The inlet 104 to the electrode terminal chamber is in communication with a flow channel 108, for receiving fluids aspirated from a surgical site. The fluid flowing through the electrode terminal chamber 102 generally comprises an electrically conductive saline solution. The electrode terminal chamber 102 further includes first and second electrode terminals 130 and 140 arranged opposite one another in a spaced-apart relationship, which accordingly generate at least one electrical signal indicative of the flow rate of the fluid flowing through the electrode terminal chamber 102. The flow of fluids through terminal chamber of housing 100 can be detected by a Hall effect sensor in a console 200, shown in FIG. 2. The flow of fluids through the housing 100 is preferably received within a collection cassette 206. The Hall-effect sensor is not shown in FIG. 1, but is described in U.S. Pat. Nos. 6,599,277 and 6,634,237, both of which are assigned to the current assignee of the present application, and incorporated herein by reference. The Hall-effect sensor is operatively positioned relative to the electrodes 130 and 140.

Figure 2:
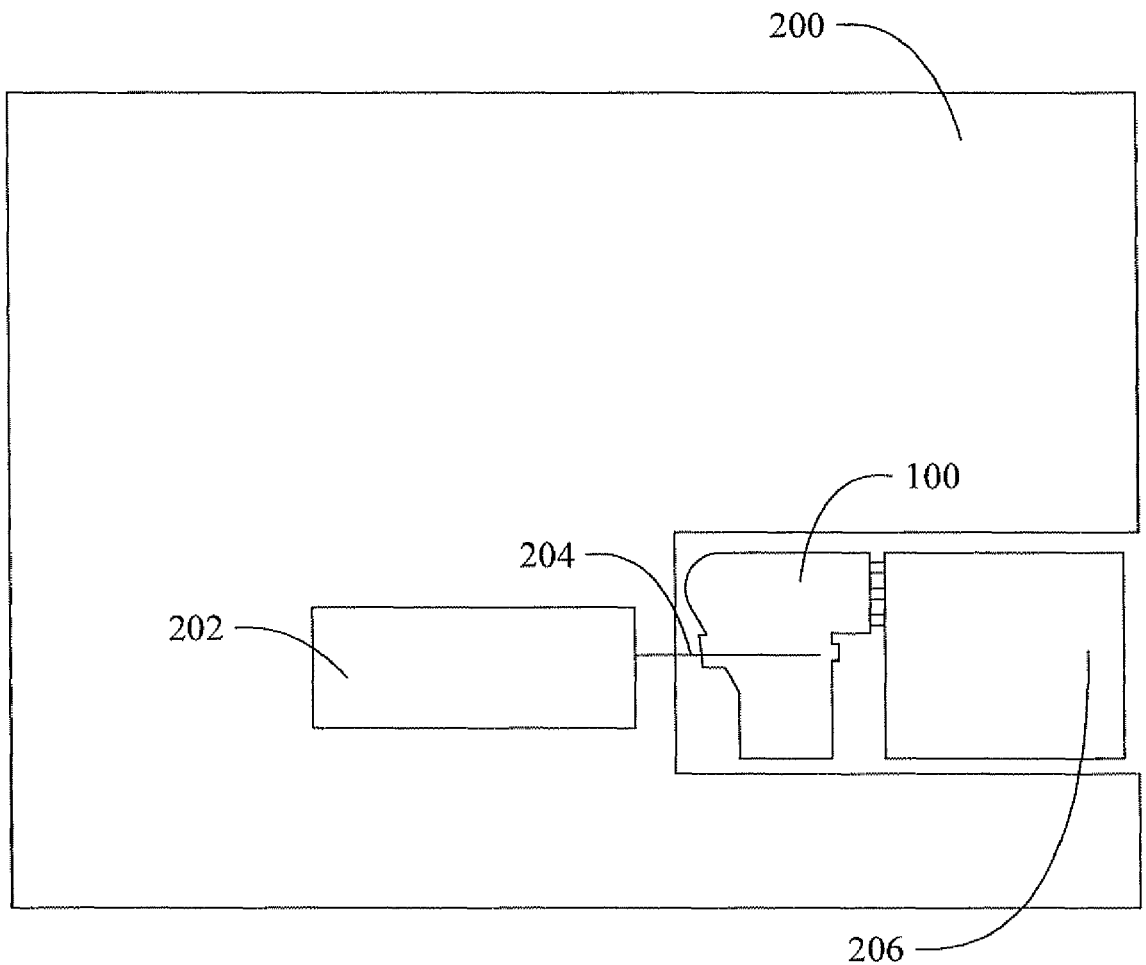
FIG. 2 shows a console including an aspiration flow measurement sensor according to the principles of the present disclosure.

As shown in FIG. 2, the electrodes and Hall-effect sensor are connected to a processor 202 via connection 204. Air bubbles within the fluid disrupt the sensor signal because the Hall-effect sensor relies on electrical conductivity through the fluid between the two electrodes. Small bubbles can create signal disturbances by distorting the electric field path between the electrodes. Similarly, large bubbles can create signal disturbances by breaking the conductivity or path between the electrodes. It should be noted that neither effect depends on the magnitude of the signal.

According to one aspect of the present application, a flow measurement control system is configured to identify the presence of air bubbles in the aspirated fluid flow, or to detect a portion of a flow measurement signal that is reflective of an air bubble in the aspirated fluid flow. Those portions or segments of the aspiration flow signal that are generated when an air bubble is present or near the flow sensing electrode terminals 130 and 140 may cause an erroneous spike in the sensed flow rate signal, as shown in FIG. 3.

Figure 3:
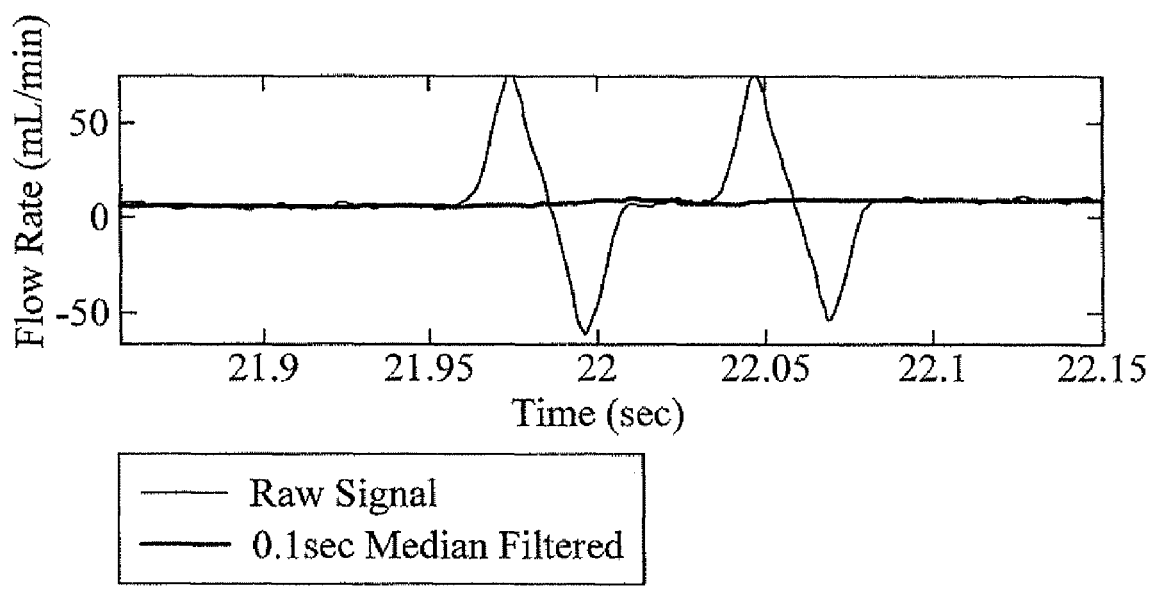
FIG. 3 shows a graph of an aspiration flow measurement signal reflecting a nominal flow rate and an occurrence of a disruption.
Figure 4:
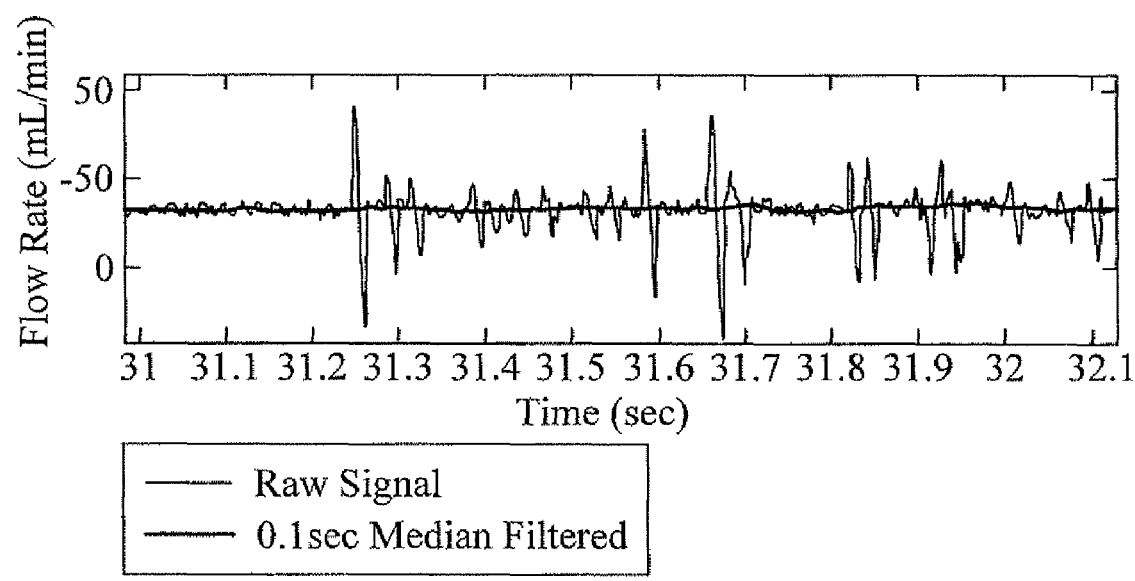
FIG. 4 shows a graph of an aspiration flow measurement signal reflecting a number of flow disruption occurrences.

Referring to FIG. 3, a graph of an aspiration flow measurement signal reflecting a nominal flow rate above zero ml/min is shown. The portion of the aspiration flow signal that begins at approximately 21.95 seconds and ends at approximately 22.1 seconds includes an anomalous spike that exceeds a flow rate of 50 ml/min. This signal spike is indicative of the presence of an air bubble that is present at or near the flow chamber 102.

Where possible, the flow measurement control system is configured to remove the artifact or erroneous portion of the flow signal that is generated when an air bubble is present or near the flow chamber 102. Such removal enables a filtered signal to be provided, as shown in FIG. 4. The filtered signal is not affected by any spikes found within the raw signal (shown in FIG. 4) that is generated by the aspiration flow measurement means.

Figure 5:
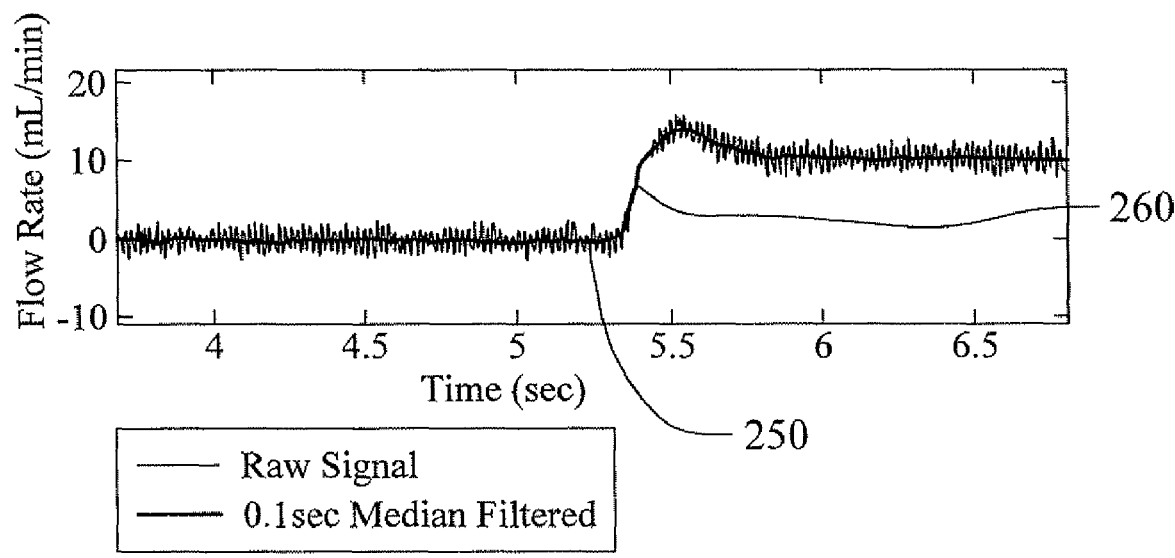
FIG. 5 shows a graph of a raw aspiration flow measurement signal and a filtered flow measurement signal according to the principles of the present disclosure.

This feature is significant because air bubbles can cause surge or compliance problems, or indicate a loose fitting. Detecting signal disruptions associated with air bubbles therefore allows for safer ophthalmic surgical procedures. In addition, providing flow signal errors or artifacts due to the presence of bubbles enables any control system that relies on a flow meter signal to operate more robustly, since the raw signal 250 is converted to a filtered signal 260 that accurately reflects rises in the flow rate without the effect of spikes or fluctuations in the raw signal 250 shown in FIG. 5.

Figure 6:
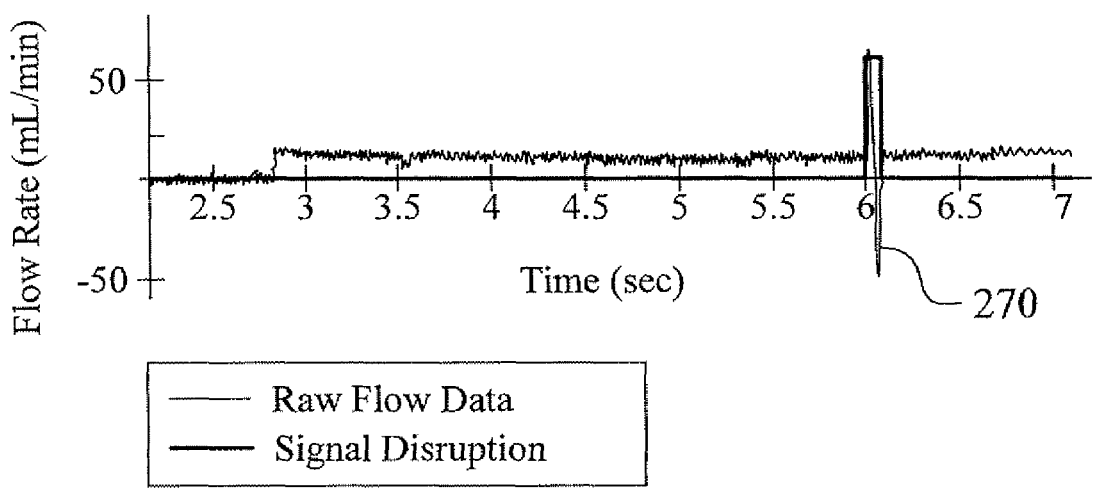
FIG. 6 shows a graph of an aspiration flow measurement signal with a disruption, and a filtered flow measurement signal according to the principles of the present disclosure.

According to another aspect of the present disclosure, an algorithm for detecting and removing erroneous portions of an aspiration flow measurement signal is provided. The algorithm essentially deals with signal disruptions due to air bubbles by processing the signal using a filter. In the first embodiment of a flow measurement control system, the control system or algorithm employs a median filter of approximately 0.1 second long, as shown in FIG. 6, in which period a disruption is shown at 270. The above median filter was found to be effective to remove disruptions due to all but the largest air bubbles. The 0.1 second median filter also can handle several bubbles in rapid succession. In addition, the filter smoothes out the noise in the flow signal, which is mostly due to interference caused by the alternating current line voltage.

Figure 8:
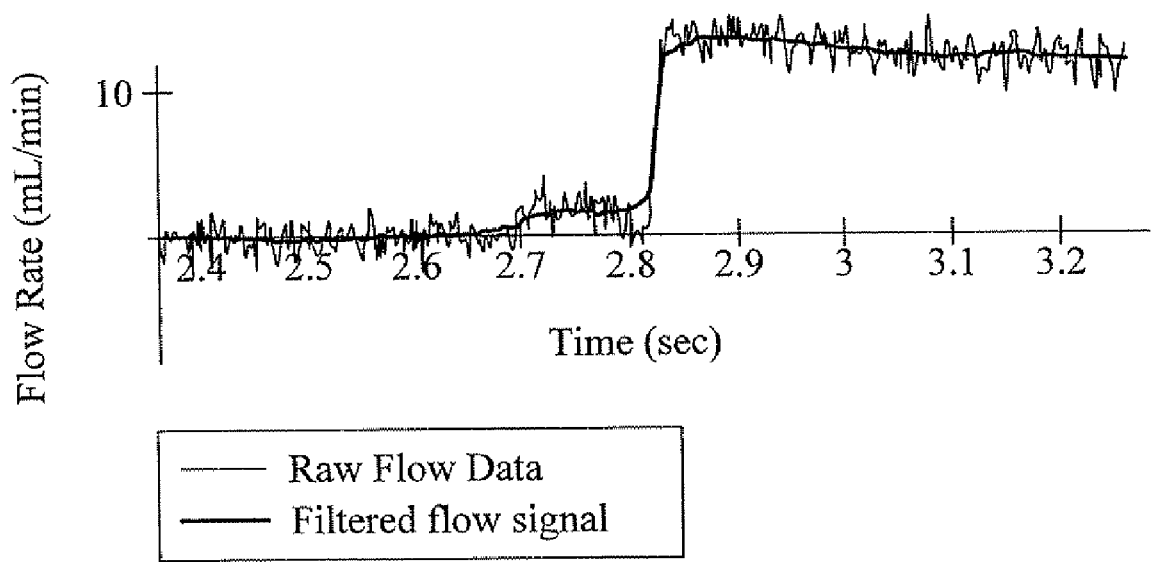
FIG. 8 shows a graph of an aspiration flow measurement signal in which signal values indicate a high rate of increase or step in flow rate, according to the principles of the present disclosure.

The above disclosed embodiment employs a median filter rather than a linear average filter, but a linear averaging filter could also be employed, or combinations of median filtering and averaging. For example, the algorithm could average the signal data window between the 40th and 60th percentiles of the flow rate's value. The 0.1 second median filter in the first embodiment is the preferred filter embodiment, given that it responds quickly to signal disruptions or monotonic transients (e.g.—steps in the flow as shown in FIG. 8).

In addition, the algorithm of the first embodiment detects a signal disruption based on setting a threshold for a quantity calculated from the signal size, the rate of change with time (first derivative) and the acceleration (second derivative). The rate of change with time and acceleration are calculated in a manner that is robust to noise, as described below. In normal operation, any one of the signal size, signal rate of change and signal acceleration may assume a large value. The calculated quantity is chosen to yield a large value (in excess of the threshold) when all three signals jointly assume exceptional values.

With regard to the control system's signal processing, the raw flow measurement signal in the first embodiment is preferably sampled or output at 500 Hz. At every measured sample, a quadratic function is fitted to a window of 10 samples. The window of 10 samples corresponds to an alternating current cycle (at 50 Hz), and is therefore not sensitive to sinusoidal fluctuations due to waveform crossing of the main or line voltage source. The fit produces coefficients c0 (a constant term), c1 (a linear term) and c2 (a quadratic term), which are put into a 3×1 vector matrix:

$$c = \begin{pmatrix} c0 \\ c1 \\ c2 \end{pmatrix}$$

In a calibration process, the average value of c, $\overline{C}$, and its covariance matrix C are calculated from data representing normal operating conditions (i.e.—with normal flow transients and no signal disruptions). Typically, $\overline{C}$ can be set to zero and C to the diagonal matrix below:

$$C = \begin{pmatrix} n^2 & 0 & 0 \\ 0 & (nf)^2 & 0 \\ 0 & 0 & (nf^2)^2 \end{pmatrix}$$

where n is the typical noise amplitude of the measured flow signal and f is a characteristic frequency related to the window length for the quadratic fit (window of 10 samples corresponding to 50 Hz).

A signal disruption was determined to occur when:

$$\sigma = \sqrt{(c-\overline{C})^T C^{-1}(c-\overline{C})} \geq 3 \quad (1), \text{ or}$$

$$C0 < \text{zero} \quad (2)$$

where the first condition (1) identifies when the signal differs from normal behavior by more than three standard deviations, and the second condition (2) identifies when the flow measurement is negative. The first condition (1) accordingly sets a signal amplitude threshold, beyond which a signal disruption is determined to have occurred. The second condition (2) indicates a signal disruption because negative flows are not expected in the aspiration flow application for ophthalmic surgical procedures. However, this second condition (2) could be removed where negative or reverse flow conditions could occur in other applications.

A control system may utilize the above signal processing equations for determining the occurrence of a disruption when a value exceeds a threshold. Alternatively, the control system may determine the occurrence of a disruption upon detecting an unusually high flow rate, an unusually high rate of change of flow rate, and an unusually high second derivative, or combinations thereof.

Preferably, the control is configured to calculate a filtered signal based on a predetermined number of signal sample values falling within a predetermined time period, where any signal value samples that are indicative of an air bubble disruption are excluded such that the filtered signal is based on the remaining signal value samples within a predetermined time. In the preferred embodiment, a window of 50 samples is used to calculate the filtered signal. Those samples for which a signal disruption is determined to have occurred are excluded, and the filtered signal is the median of the remaining samples. If all of the 50 samples are determined to be disruptions, such that the median filter has no data during the disruption to operate with, an error signal may be output. Thus, where a long signal disruption occurs, the control system is configured to output an error signal.

Figure 7:
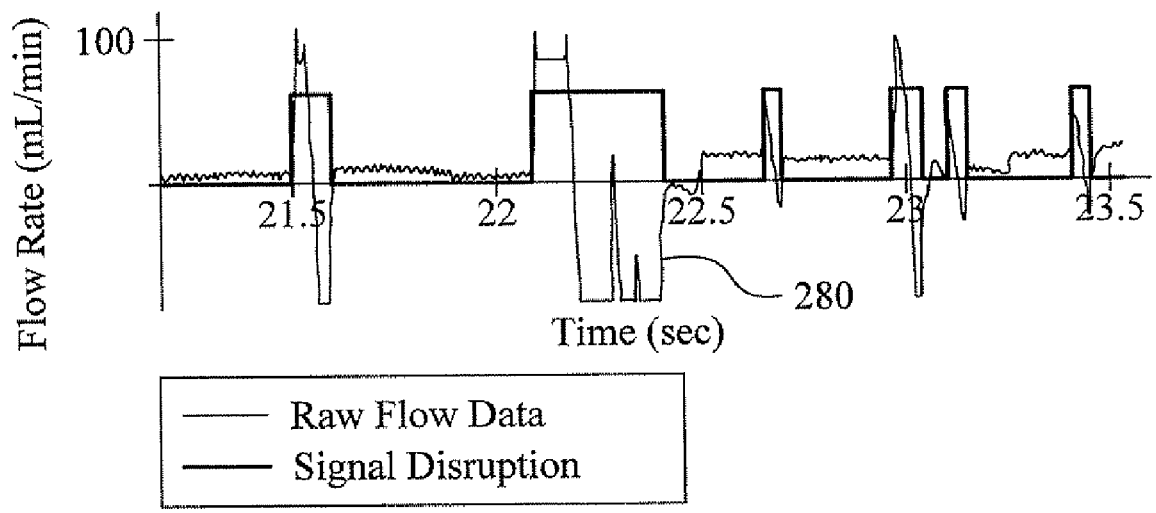
FIG. 7 shows a graph of an aspiration flow measurement signal with a disruption that exceeds a predetermined time period according to the principles of the present disclosure.

Referring to FIG. 7, when the aspiration flow measurement signal includes signal disruptions 280 that last longer than the median window length of 0.1 seconds, the median filter will not be able to remove the disruption. In this case, the algorithm generates an error signal that will be output when a large proportion of the 0.1 second window has a signal disruption. The use of a median filter delays the output of the filtered signal, such that erroneous signal samples can be excluded. For a median window of 50 samples (used in calculating the filter signal), the filtered signal is delayed from the raw signal by 25 samples, i.e. by 0.05 seconds. This time response of the median filter has particularly been found to be very good for transients that are monotonic over the window, e.g. for step functions or stepped increases in flow rates. Oscillations with a period equal to the window size or less are strongly attenuated. For a window of 50 samples, this means that oscillations at 10 Hz and higher are attenuated. Similarly, a signal spike of less than 25 samples, or a duration of 0.05 samples, are ignored.

When the flow algorithm outputs an error signal, the control system can respond to the error signal, and go into a safe mode, in one of two ways. Over the short term period (e.g. <1 second), the algorithm or control system can assume that the system has a fixed fluidic resistance, and assume a constant of proportionality between pressure and flow in applying a pressure. The pressure is proportional to the flow rate demanded by the system (or a surgeon). In determining a pressure, the lowest observed flow resistance measured during a preceding time period (e.g. the last 30 seconds or the last minute) would be a reliable value to use, and would not generate excessive pressure. Over the long term period (e.g. >1 second), the control system can revert to vacuum mode, and alert the surgeon of the flow measurement error and switch to vacuum mode.

Figure 9:
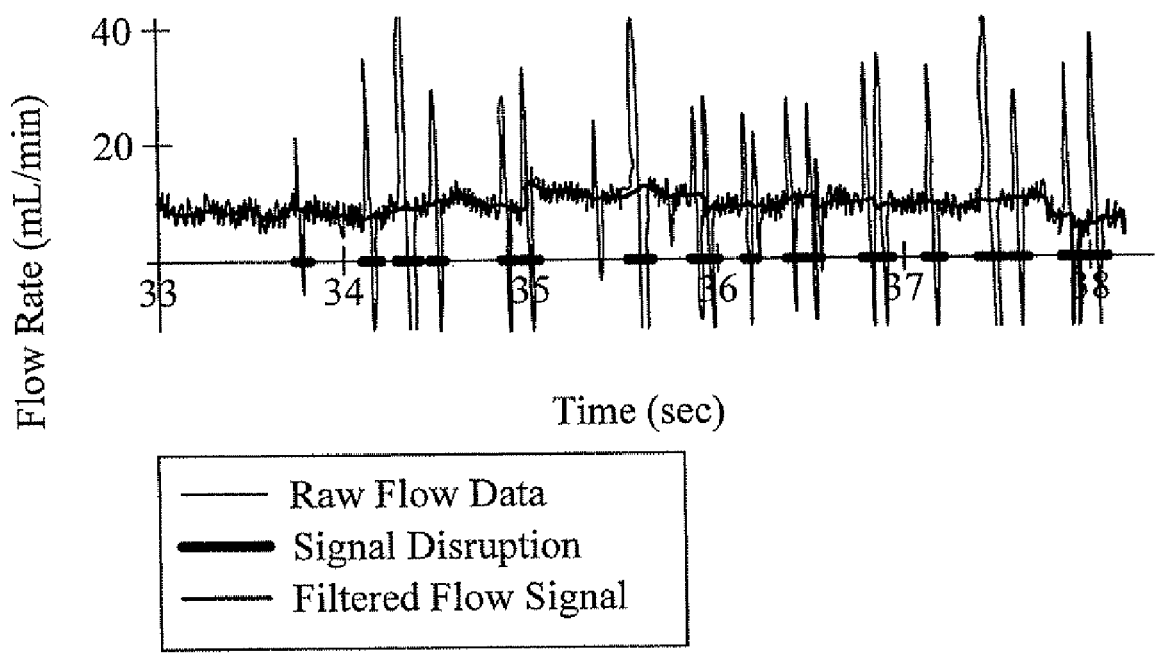
FIG. 9 shows a raw data signal having numerous spiked signal values associated with air bubble disruptions, which are excluded from a calculated filtered signal during disruption periods.
Figure 10:
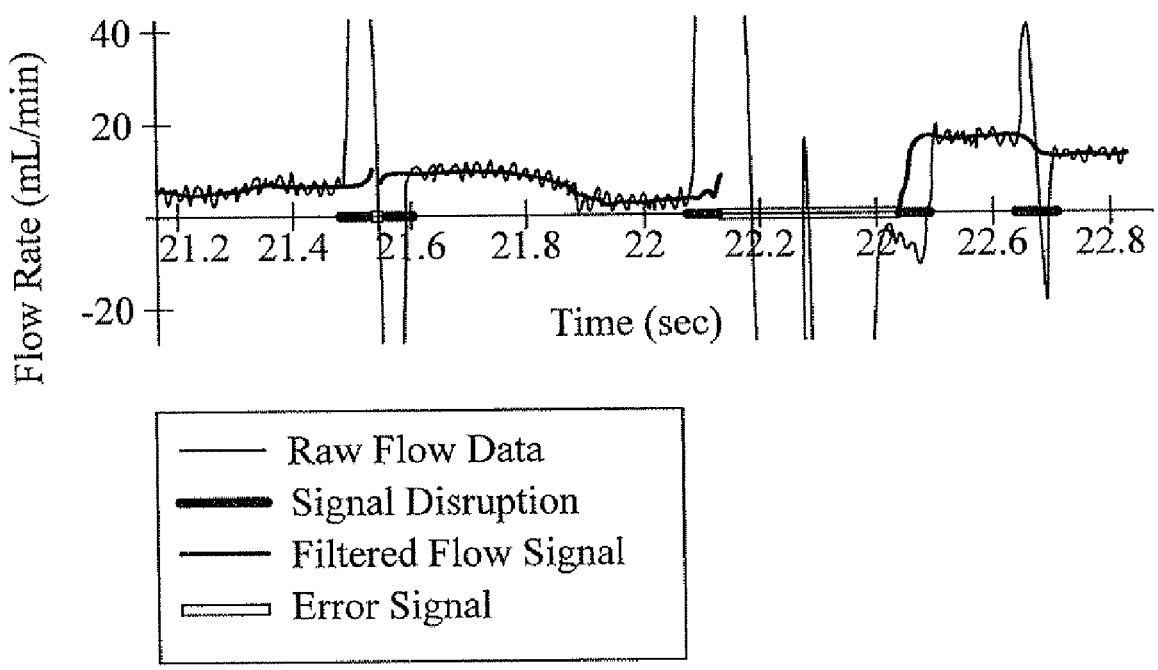
FIG. 10 shows a raw data signal having numerous spiked signal values associated with air bubble disruptions that are excluded from a filtered signal, where an error signal is output during disruptions greater than a predetermined time period.

FIGS. 8 through 10 show examples of the results of the algorithm and control system. In FIG. 8, signal values indicative of a high rate of increase, or which exceed a threshold, cause the control system or algorithm to determine a disruption where an abrupt increase in flow rate is called for. FIG. 9 shows a raw data signal having oscillations and numerous spikes, where the spikes are associated with an air bubble. The control system or algorithm detects and excludes signal values associated with the spikes to provide or output a filtered signal, as shown in FIG. 9.

The control system is preferably configured to generate a signal indicative of an air bubble disruption during the occurrence of a number of consecutive signal samples that exceed the predetermined threshold. Referring to FIG. 10, the control system or algorithm may detect signal values that exceed a threshold or are indicative of a high rate of increase, and exclude such signal values from the calculation of the filtered signal, to provide a filtered signal that does not significantly change during the spike. The portions of the raw signal that have been determined to be disruptions are indicated by the heavy solid bar 290 along the horizontal time axis.

The control system is also configured to generate an error signal upon detecting a number of signal samples that are indicative of an air bubble disruption, which number of signals last for more than a predetermined time period. Where the disruption is greater than a predetermined time period or window of sample measurements, the control system outputs an error signal that is indicated in FIG. 10 by the outlined bar 295 on the horizontal time axis.

Figure 11:
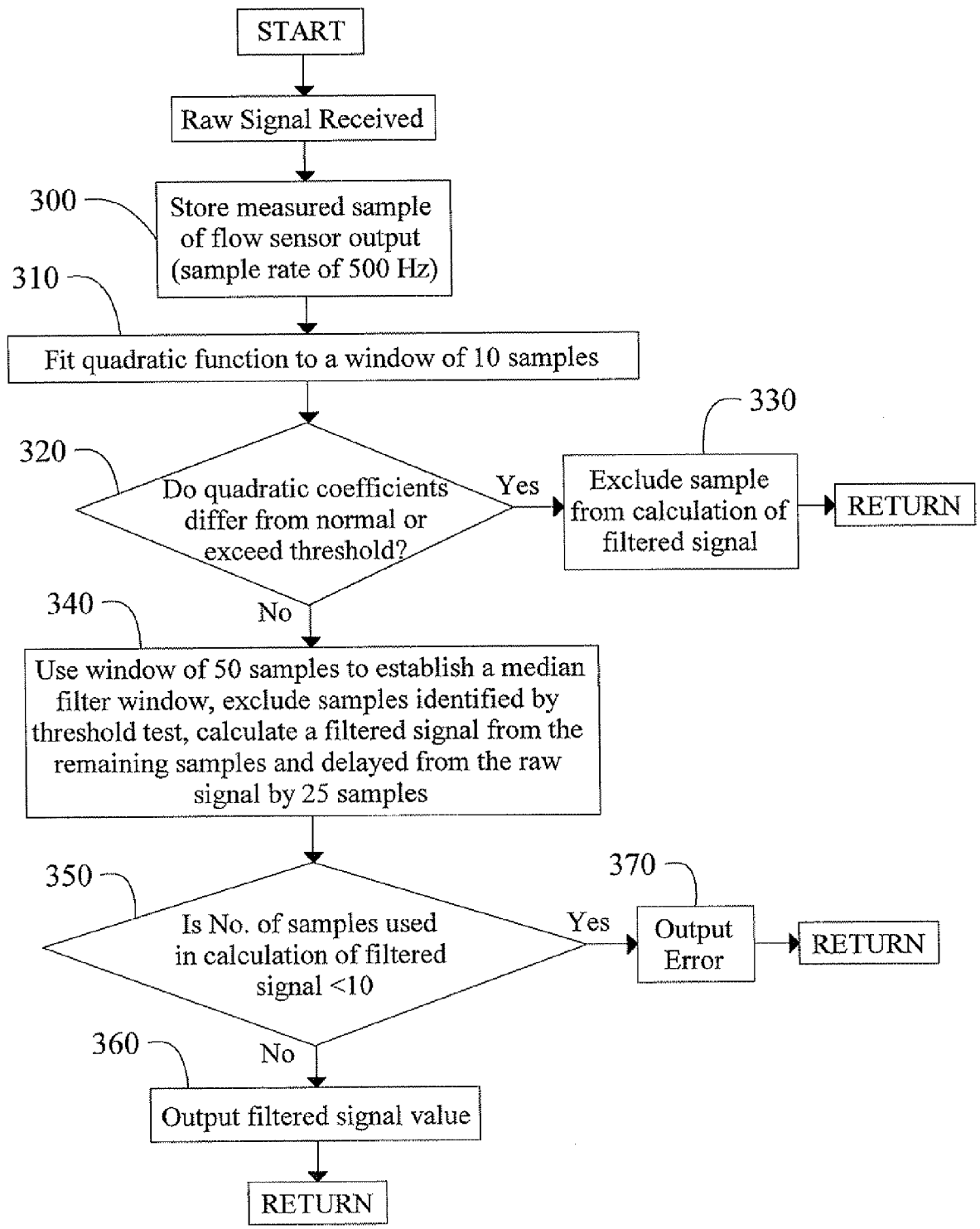
FIG. 11 shows a flow chart of a method for filtering a flow measurement signal in accordance with the principles of the present disclosure.

Referring to FIG. 11, a flow chart of logic that can be implemented by the processor 202 is shown. The start of the flow chart represents the receipt of raw sensor signal information, where signal sampling is acquired at a frequency of 500 Hz. At step 300, the flow chart stores an acquired raw signal sample value from a flow sensor. At step 310, a quadratic function may be fit to, for example, the 10 most recent stored samples. At step 320, the algorithm may determine whether a raw signal value has exceeded a threshold, such that the erroneous signal value can be excluded from the calculation in step 330.

If a raw signal sample is determined to exceed a threshold as explained above, the raw signal sample is marked or otherwise excluded in step 340 from the calculation of a filtered signal. At step 340, the logic chart or algorithm uses, for example, a window of 50 samples (median filter of 0.1 second based on 500 Hz sample rate) to establish a median filter window, and calculates a filtered signal based on the 50 sample window. The filtered signal calculated based on a window of 50 samples is delayed from the raw signal by 25 samples, and excludes any erroneous sample values exceeding a threshold that are indicative of a disruption caused by the presence of an air bubble, for example. At step 350, the algorithm determines whether the number of consecutive signal samples that exceed a threshold is greater than 50 samples. If less than 50, a filtered signal based on samples that do not exceed the threshold is output at step 360. Where the number of consecutive signal samples exceeds 50 (e.g.,—a signal disruption lasts longer than the median window length of 50 samples or 0.1 seconds), an error signal is output at step 370. The above steps provide for elimination of erroneous signal values from the calculation of a filtered signal, and for reporting an error signal upon the occurrence of 50 consecutive signal sample values that may be caused by the presence of an air bubble, for example.

As shown in FIG. 10, when a signal disruption is detected, the disruption is indicated by a heavy solid bar 290 on the time axis, and an error signal is indicated by a clear bar 295 on the time axis.

Using the above process, oscillations within a period equal to the window size or less are strongly attenuated. For example, with a window of 50 samples, oscillations at a frequency of 10 Hz and higher are attenuated. Signal spikes of less than 25 samples are excluded and ignored. Accordingly, the above process may be included in a method for filtering an aspiration flow measurement signal. The method entails receiving an aspiration fluid flow through a flow channel, and generating a raw signal indicative of the rate of fluid flow through the flow channel. The method includes the step of monitoring the raw signal generated by the aspiration flow sensor, to determine when a signal value is indicative of a disruption caused by the presence of an air bubble based on when the signal value exceeds a predetermined threshold. In accordance with the method, a control preferably monitors the raw signal. The method includes the step of the control generating a filtered signal indicative of the flow rate that is exclusive of any signal values that are indicative of a disruption. The method or control may be configured to generate a signal indicative of an air bubble disruption during the occurrence of a number of consecutive signal samples that exceed the predetermined threshold. The method or control may be configured to generate an error signal upon detecting a number of signal samples that are indicative of an air bubble disruption lasting more than a predetermined time period.

Figure 12:
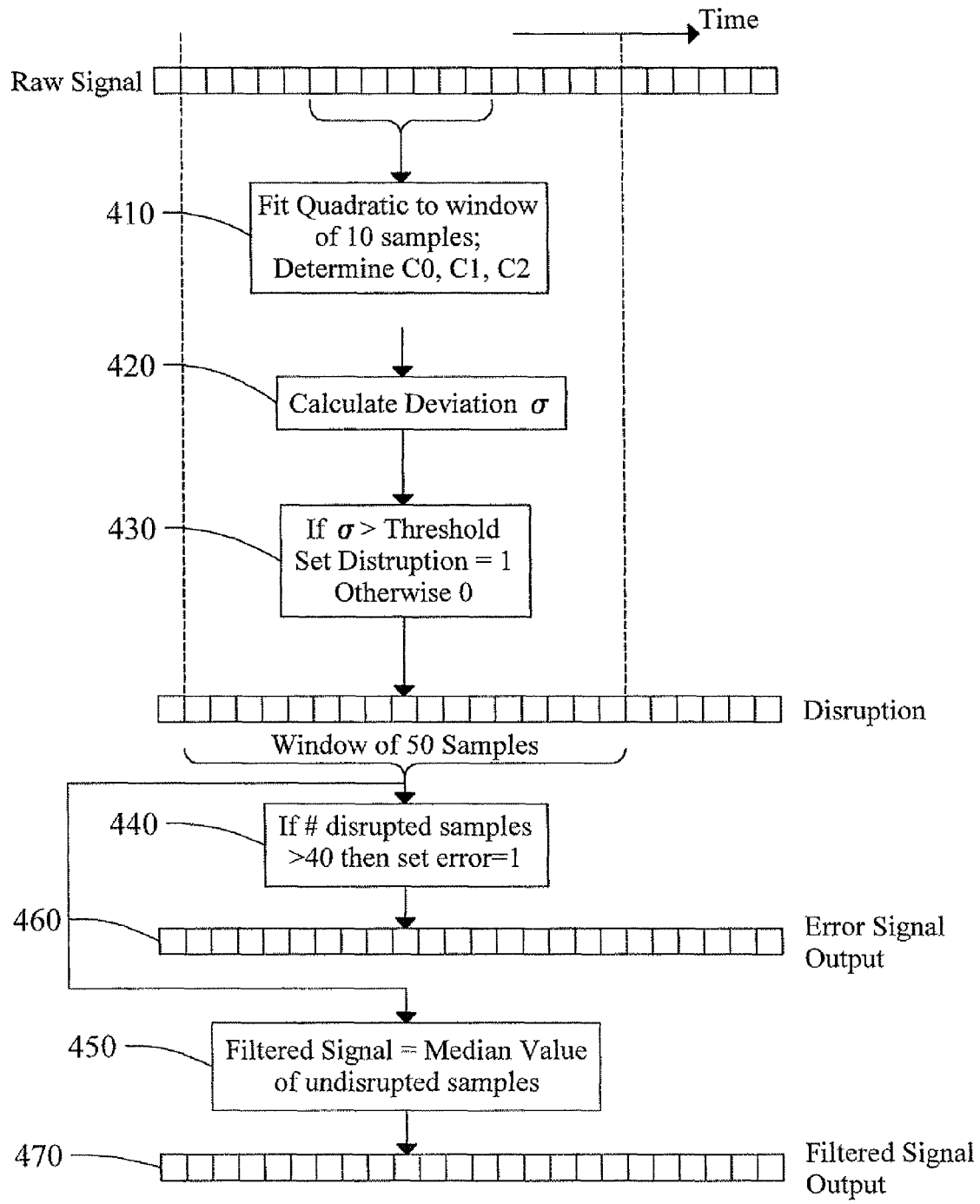
FIG. 12 shows a signal diagram illustrating an alternate logic method for filtering a flow measurement signal in accordance with the principles of the present disclosure.

Referring to FIG. 12, a signal diagram is shown that illustrates an alternate logic method that can be implemented by the controller or processor. The method first fits a quadratic function to a select window of "N" samples at step 410, to determine variables C0, C1, and C2, and then calculates at step 420 the deviation associated with a sample within the window. Where a threshold has been exceeded at step 430, such as when the calculated deviation differs from normal behavior by more than three standard deviations, a disruption value is set=to 1 for a given sample; otherwise the disruption value is set to 0. The method then determines at step 440 whether the number of disrupted samples within a window of 50 samples is greater than 40, and responsively sets an error value=to 1. At step 450, a filtered signal is determined based on the median value of undisrupted samples within a median window of N samples, which may be 50 samples for example. An error signal is output where the number of disrupted samples exceeds 40 in step 460, otherwise a filtered signal is output at step 470. It should be noted that the error signal is output when there are too few un-disrupted samples within the 50 sample median filter to reliably determine a median value, and that the excluded disrupted samples need not be consecutive to result in an error signal.

From the above, it may be appreciated that the present invention provides an improvement to aspiration flow control, in configuring first and second flow channels to separate air bubbles from the stream of fluid flow to thereby restrict the passage of air bubbles to an aspiration flow measurement means. The present invention is illustrated herein by example, and various modifications may be made by a person of ordinary skill in the art.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An aspiration flow measurement system for an ophthalmic microsurgical system comprising:
   a flow channel for receiving an aspiration fluid flow therethrough;
   an aspiration flow measurement apparatus configured to generate a signal indicative of the rate of fluid flow through the flow channel; and
   a control system configured to monitor the signals generated by the aspiration flow measurement apparatus, and to determine when a signal value is indicative of a disruption caused by the presence of an air bubble, wherein the control system generates a filtered signal indicative of the flow rate that is exclusive of any signal values that are indicative of a disruption.

2. The aspiration flow measurement system of claim 1, wherein the control system is configured to determine when a signal value is indicative of the disruption caused by the presence of the air bubble, based on when the signal value exceeds a predetermined threshold.

3. The aspiration flow measurement system of claim 2, wherein the control system is configured to determine when a signal value is indicative of a sensed flow rate that exceeds a predetermined value.

4. The aspiration flow measurement system of claim 1, wherein the control system is configured to determine when a signal value is indicative of a sensed rate of change that exceeds a predetermined value.

5. The aspiration flow measurement system of claim 1, wherein the filtered signal is based on a predetermined number of signal sample values falling within a predetermined time period, where any signal value samples that are indicative of the air bubble disruption are excluded such that the filtered signal is based on the remaining signal value samples within a predetermined time.

6. The aspiration flow measurement system of claim 1 wherein the control system is configured to generate an error signal indicative of the air bubble disruption upon detecting the occurrence of a number of consecutive signal samples that exceed the predetermined threshold.

7. The aspiration flow measurement device of claim 1 wherein the control system is configured to determine when more than a predetermined number of signal values within a given time period are indicative of the air bubble disruption, and to responsively output an error signal.

8. The aspiration flow measurement system of claim 1, wherein an algorithm of the control system fits a quadratic function to a set of signal value samples, and determines when a signal value is indicative of the air bubble disruption based on when the signal differs from the average of the set of signal values by more than a predetermined number of standard deviations.

9. The aspiration flow measurement system of claim 1 wherein the control system is configured to determine when a number of signal values indicative of the air bubble disruption occurs for more than a second, and to responsively revert to a vacuum mode and output an error signal to alert a surgeon of the disruption.

10. An aspiration flow measurement system for an ophthalmic microsurgical system comprising:
    a flow channel for receiving an aspiration fluid flow therethrough;
    an aspiration flow sensor configured to generate a signal indicative of the rate of fluid flow through the flow channel; and
    a control system configured to monitor the signals generated by the aspiration flow sensor, and to determine when a signal value is indicative of a disruption caused by the presence of an air bubble, based on when the signal value exceeds a predetermined threshold, wherein the control system generates a filtered signal indicative of the flow rate that is exclusive of any signal values that are indicative of a disruption.

11. The aspiration flow measurement system of claim 10, wherein the control system is configured to determine when a signal value is indicative of a sensed flow rate that exceeds a predetermined value.

12. The aspiration flow measurement system of claim 10, wherein the control system is configured to determine when a signal value is indicative of a sensed rate of change that exceeds a predetermined value.

13. The aspiration flow measurement system of claim 10, wherein the filtered signal is based on a predetermined number of signal sample values falling within a predetermined time period, where any signal value samples that are indicative of the air bubble disruption are excluded such that the filtered signal is based on the remaining signal value samples within a predetermined time.

14. The aspiration flow measurement system of claim 10 wherein the control system is configured to exclude signal values indicative of the air bubble disruption, where the signal values fall within a predetermined time period.

15. The aspiration flow measurement system of claim 10 wherein the control system is configured to generate an error signal indicative of the air bubble disruption upon detecting the occurrence of a number of consecutive signal samples that exceed the predetermined threshold.

16. The aspiration flow measurement device of claim 10 wherein the control system is configured to determine when more than a predetermined number of signal values within a given time period are indicative of the air bubble disruption, and to responsively output an error signal.

17. The aspiration flow measurement system of claim 10, wherein an algorithm of the control system fits a quadratic function to a set of signal value samples, and determines when a signal value is indicative of the air bubble disruption based on when the signal differs from the average of the set of signal values by more than a predetermined number of standard deviations.

18. A method for filtering an aspiration flow measurement signal that is provided by an ophthalmic microsurgical system, the method comprising:
 receiving an aspiration fluid flow through a flow channel;
 generating a raw signal indicative of the rate of fluid flow through the flow channel;
 monitoring the raw signal generated by the aspiration flow sensor to determine when a signal value is indicative of a disruption caused by the presence of an air bubble, based on when the signal value exceeds a predetermined threshold; and
 generating a filtered signal indicative of the flow rate that is exclusive of any signal values that are indicative of a disruption.

19. The method of claim 18 further comprising the step generating a signal indicative of the air bubble disruption upon detecting the occurrence of a number of consecutive signal samples that exceed the predetermined threshold.

20. The method of claim 18 further comprising the step of generating an error signal upon detecting a number of signal samples that are indicative of the air bubble disruption lasting more than a predetermined time period.

* * * * *